(12) United States Patent
Lavallee

(10) Patent No.: US 8,880,152 B2
(45) Date of Patent: *Nov. 4, 2014

(54) SYSTEM FOR DETERMINING THE POSITION OF A KNEE PROSTHESIS

(71) Applicant: Perception Raisonnement Action en Medecine, La Tronche (FR)

(72) Inventor: Stephane Lavallee, Saint Martin d'Uriage (FR)

(73) Assignee: Perception Raisonnement Action en Medecine, La Tronche (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/148,333

(22) Filed: Jan. 6, 2014

(65) Prior Publication Data

US 2014/0188121 A1      Jul. 3, 2014

Related U.S. Application Data

(63) Continuation of application No. 13/404,358, filed on Feb. 24, 2012, now Pat. No. 8,626,267, which is a continuation of application No. 10/415,962, filed as application No. PCT/FR01/03423 on Nov. 6, 2001, now Pat. No. 8,126,533.

(51) Int. Cl.
*A61B 5/05*      (2006.01)
*A61F 2/46*      (2006.01)
*A61B 19/00*     (2006.01)

(52) U.S. Cl.
CPC ........... *A61F 2/4657* (2013.01); *A61B 19/5244* (2013.01); *A61B 19/50* (2013.01)
USPC ....................................... 600/424

(58) Field of Classification Search
USPC .......................................... 600/424, 427–429
See application file for complete search history.

(56) References Cited

U.S. PATENT DOCUMENTS 5,564,437 A    10/1996   Bainville et al.
5,682,886 A    11/1997   Delp et al.

(Continued)

FOREIGN PATENT DOCUMENTS

EP    0920838     9/1999
FR    2775889     9/1999

(Continued)

OTHER PUBLICATIONS

Office Action issued Oct. 7, 2011 in U.S. Appl. No. 11/955,160.

(Continued)

*Primary Examiner* — Sameh Boles
(74) *Attorney, Agent, or Firm* — Kim Winston LLP

(57) ABSTRACT

The present application provides an apparatus and method for determining a position of a joint prosthesis using a computer assisted orthopedic surgery system in support of an arthroplasty surgery. The apparatus and method includes attaching a first locatable element to a first bone on one side of a joint, providing a sensor having a second locatable element and moving the sensor in proximity of the joint to locate a plurality of positions of the sensor relative to the first locatable element using a tracking device. The apparatus and method further includes selecting a generic model of a joint, determining the generic model in response to the plurality of positions located using the tracking device to generate a deformed model determining a position for a joint prosthesis on the deformed model, and outputting on a display the determined position upon the deformed model.

22 Claims, 9 Drawing Sheets

(56) References Cited

U.S. PATENT DOCUMENTS

| | | | |
|---|---|---|---|
| 5,722,978 | A | 3/1998 | Jenkins, Jr. |
| 5,880,976 | A | 3/1999 | DiGioia, III et al. |
| 6,021,343 | A | 2/2000 | Foley et al. |
| 6,205,411 | B1 | 3/2001 | DiGioia, III et al. |
| 6,385,475 | B1 | 5/2002 | Cinquin et al. |
| 6,466,815 | B1 | 10/2002 | Saito et al. |
| 6,533,737 | B1 | 3/2003 | Brosseau et al. |
| 6,554,837 | B1 | 4/2003 | Hauri et al. |
| 6,608,628 | B1 | 8/2003 | Ross et al. |
| 6,711,432 | B1 | 3/2004 | Krause et al. |
| 6,725,082 | B2 | 4/2004 | Sati et al. |
| 7,227,981 | B1 | 6/2007 | Fleute et al. |
| 7,689,014 | B2 | 3/2010 | Abovitz et al. |
| 7,715,602 | B2 | 5/2010 | Richard |
| 7,799,077 | B2 | 9/2010 | Lang et al. |
| 7,842,092 | B2 | 11/2010 | Otto et al. |
| 7,881,768 | B2 | 2/2011 | Lang et al. |
| 2004/0015070 | A1 | 1/2004 | Liang et al. |
| 2006/0015030 | A1 | 1/2006 | Poulin et al. |
| 2006/0039591 | A1 | 2/2006 | Zettel et al. |
| 2006/0095047 | A1 | 5/2006 | de la Barrera |
| 2008/0077003 | A1 | 3/2008 | Barth et al. |

FOREIGN PATENT DOCUMENTS

| | | |
|---|---|---|
| FR | 2785517 | 5/2000 |
| WO | 9500075 | 1/1995 |
| WO | 9840037 | 9/1998 |
| WO | 9923956 | 5/1999 |
| WO | 9960939 | 12/1999 |

OTHER PUBLICATIONS

Office Action issued Mar. 31, 2011 in U.S. Appl. No. 11/955,160.
<http://en.wikipedia.org/wiki/Levenberg-Marquardt_algorithm>, last modified Mar. 1, 2012.
Fleute, M., et al., "Incorporating a statistically based shape model into a system for computer-assisted anterior cruciate ligament surgery," Medical Image Analysis, (1999), 3(3): 209-222.
International Search Report dated Mar. 1, 2002 for International App. PCT/FR01/03423.
Kienzle T C et al. "Total Knee Replacement" IEEE Engineering in Medicine and Biology Magazine, IEEE Inc. NY, NY vol. 14, No. 3 (May 1, 1995) pp. 301-306.
Fleute, M. et al. "Building a complete surface model from sparse data using statistical shape models: Application to Computer Assisted Knee Surgery." MICCAI 1998 Springer-Verlag LNCS Series, pp. 880-887, Oct. 1998.
Fleute, M. et al. "Nonrigid 3D/2D registration of images using statistical models" MICCAI '99, Springer-Verlag LNCS Series 1679, pp. 138-147, Oct. 1999.
Taylor, R. "Computer Integrated Surgery" Chapter 32, MIT Press 1996, entitled "Computer-assisted spinal surgery using anatomy-based registration" pp. 434-437 by Lavallee, S., et al.
Office Action issued Oct. 6, 2010 in U.S. Appl. No. 10/415,962.
Office Action issued May 26, 2010 in U.S. Appl. No. 10/415,962.
Stryker, "Precision Knee Navigation System," 2007, 4 pages, USA.

SYSTEM FOR DETERMINING THE POSITION OF A KNEE PROSTHESIS

CROSS-REFERENCE TO RELATED APPLICATIONS

This application is a continuation of U.S. patent application Ser. No. 13/404,358 filed Feb. 24, 2012, which is a continuation of U.S. patent application Ser. No. 10/415,962 filed Oct. 22, 2003, now U.S. Pat. No. 8,126,533, which is a 371 national phase of International Application No. PCT/FR01/03423 filed Nov. 6, 2001, which is entitled to and claims the benefit of foreign priority under 35 U.S.C. §119 to French Patent Application No. 00/14173, filed Nov. 6, 2000, the entire disclosures of which are hereby incorporated herein by reference.

The present invention relates to a system for determining the position of a prosthesis enabling assisting a surgeon in the fitting of knee prostheses, by means of the computer system present at the operating suite.

The general aim of computer-assisted knee surgery is to determine an optimal position of the prostheses on the tibia, on the femur, and possibly on the patella according to geometric and dynamic criteria, and to provide devices enabling effective placing of the prostheses at the optimal place. Ideally, an alignment of the centers of the hip, of the knee and of the ankle is attempted to be restored for a knee placed in extension, while balancing the position of the patella and the tensions of the ligaments in a flexional motion, and while having good adjustments of the prostheses with the bones. In some cases, only a portion of the knee is replaced, for example, one of the two condyles of the femur, but the criteria remain identical.

Conventional methods use mechanical ancillaries adjustable according to the radiological data of each patient. Such methods are inaccurate and do not enable performing an ideal prosthesis fit in all cases, which sometimes leads the surgeon to progressively adjusting the positions of the prostheses, which is long and difficult, or to be content with an average quality result.

To overcome these disadvantages, computer-assisted surgery systems using position sensors, computers and possibly robots have been developed.

Generally, in conventional computer-assisted surgery systems, a remarkable element, also known as the measurement mark, to a bone or an anatomic structure and its motions are followed by means of a position sensor, also known as a locating system or a tridimensional positioning system. Such a position sensor may be a set of cameras which locate the position and orientation of measurement marks each formed of at least three infrared diodes or reflective markers. Many acoustic, mechanical, or magnetic technologies enabling locating of the relative position and orientation of two position marks attached on anatomic structures, surgical instruments, digitizing palpation devices or various sensors such as described in chapter 1 of book "Computer Integrated Surgery", MIT Press, 1996, R. Taylor ed., entitled "Multimodal Information for Computer-Integrated Surgery", pages 5-21, by R. Moesges and S. Lavallee may be used. One of the position marks may also be used as a position sensor, as is the case in small-size magnetic systems. By means of these position sensors, a palpation device may be used to digitize points on the surface of the structures equipped with, a position mark, and motions between two bones equipped with position marks may also be recorded.

Most of the existing computer-assisted surgical systems for assisting the fitting of a total knee prosthesis require use of medical images acquired before an intervention by powerful means such as the tomodensimetric (TDM) scanner or magnetic resonance imaging (MRI), as described in the patents of ORTHOSOFT Inc (WO 99/60939), Erie Brosseau et al., or of Scott Delp et al. (U.S. Pat. No. 5,682,886). Based on these images, a doctor can plan and partially simulate a surgical intervention, then complex techniques of adjustment between the patient's images and the patient's position on the operation table enable following and reproducing the planned strategies. However, the acquisition of such images in clinical routine is complicated to manage, it has a non-negligible cost, error risks are associated with the adjustment methods, and the use of a scanner generates an X-ray close which is non-negligible for the patient. Further, such systems do not use the cinematic and dynamic information which can be easily acquired at the beginning of an operation, they thus do not enable directly and easily obtaining the ideal position of the prosthesis.

An alternative consists of only using information acquired just before the beginning of the operation by means of position sensors. Such methods are however limited in their use since they only enable collecting very simple information to remain within reasonable time limits.

In this category, the most widely used methods are based on the search for an alignment of the three rotation centers of the knee, of the hip, and of the tibia, as described for example in documents WO-A-95/00075 of ANDRONIC and WO-A-98/40037 of AESCULAP. However, in such methods, the determination of the knee center is made difficult and inaccurate by the strong anatomic variations of each knee which must undergo an intervention, the very definition of a pathological knee being the subject of debates and controversies.

The present invention aims at using a simple equipment including a computer, a screen, a tridimensional positioning system, a position mark attached on each bone of the joint, and a position mark placed on a drilling guide.

An object of the present invention is to provide an automatic system for determining the best size, position and orientation for each implant laid on one or several osseous section planes, such as a conventional tibia and femur prosthesis.

Another object of the present invention is to provide such a system in which the complete surface of each bone is obtained by deformation of a generic model at the operating suite, without MRI or TDM images.

Another object of the present invention is to provide such a system in which the degree of accuracy at any point of the image of the bone surface is indicated by a color.

Another object of the present invention is to provide such a system in which ligamentary information are taken into account to balance the tensions between each bone of the knee joint.

Another object of the present invention is to provide such a system in which a drilling guide particularly simple to place to then ensure the accurate positioning of a section guide is provided.

An advantage of the present invention is that it enables avoiding determination of a knee center on the patient. Instead of aligning any center of the pathological knee with the center of the hip and of the ankle, the present invention provides aligning the center of the prosthesis of the pathological knee with the center of the hip and of the ankle.

Another advantage of the present invention is that it enables automatically determining an ideal theoretical position of all the implants to be attached on each bone, taking into account all the essential criteria and then letting the surgeon modify the parameters with respect to the so-called ideal reference, just before performing the surgical acts enabling placing the implants.

Another advantage of the present invention is that it no longer needs all the TDM or MRI methods of medical image acquisition and adjustment.

To achieve these objects, the present invention provides a system for determining the ideal theoretical position of a knee prosthesis including, for the determination of the position of a tibial prosthesis, means for:

determining the shape of the proximal portion of the tibia and its position with respect to the center of the ankle joint;
determining a high point of the superior surface of the tibia;
calculating the position, the orientation, and the size with respect to the tibia of the tibial prosthesis and of the section plane corresponding to the tibial prosthesis, taking the following parameters into account:
the perpendicular to the section plane crossing the center of the prosthesis also crosses the center of the ankle joint,
the section plane is at a distance from said high point equal to the height of the prosthesis to be attached,
the large side of the prosthesis is centered on the large side of the section of the tibia in the section plane,
the anterior edge of the small side of the prosthesis is at a predetermined distance from the anterior edge of the small side of the tibia section in the section plane; and
determining the orientation in the section plane of the prosthesis so that the large side of the prosthesis is parallel to the horizontal axis of the knee.

According to an embodiment of the present invention, the system further includes, to determine the position of a femoral prosthesis, means for:

determining the relative position of the distal portion of the femur with respect to the center of the hip joint;
calculating the position, the orientation and the size with respect to the femur of the femoral prosthesis and of the section plane corresponding to the femoral prosthesis, taking the following parameters into account:
the perpendicular to the section plane crossing the center of the prosthesis also crosses the center of the hip joint,
the distal section plane is at a distance from the most distal point on one of the condyles equal to the thickness of the prosthesis to be attached,
the posterior section plane is at a distance from the most posterior point on one of the condyles equal to the thickness of the prosthesis to be attached,
the large side of the prosthesis is centered on the large side of the section of the femur in the section plane,
the maximum size of the prosthesis is such that the edge of the prosthesis is as close as possible but inside of the femur surface; and
determining the orientation in the section plane of the prosthesis so that the large side of the prosthesis is parallel to the horizontal axis of the knee.

According to am embodiment of the present invention, the orientation and the lateral position of the femoral prosthesis are adjusted with an alignment of the plane of the trochlea of the femoral prosthesis with the trajectory of the center of the digitized patella during a knee flexion motion by means of a position mark placed on the external surface of the patella.

According to an embodiment of the present invention, this system further includes, to determine the shapes and positions of the tibia, of the femur, of the center of the ankle joint and of the center of the hip joint:

elements locatable in position in a tridimensional positioning system, attachable at least, to the tibia and to the femur, a palpation device, an echographic device, and/or a radiographic device to locate in said tridimensional positioning system the position of various points of the tibia and of the femur with respect to said locatable elements, and means for adjusting a preestablished model of the leg bones by using the collected position information.

According to an embodiment of the present invention, said model also includes a modeling of the positions of the attachments of the ligaments of the knee joint, this modeling being adapted to the patient at the same time as the model of the bone surface, and said model also includes the values of the maximum elongations of each ligament, experimentally determined by having the still non-operated patient's leg move to locate the displacement limits linked to existing ligaments.

According to an embodiment of the present invention, the system further includes means for:

simulating on the image of the femur-tibia assembly the positioning of the prostheses linked together for different flexion positions, and the position of the knee ligaments;
deducing therefrom the motion limits that the leg provided with the prosthesis will have with the existing ligaments; and
taking this information into account to modify the theoretical ideal position of the knee prosthesis, and/or to suggest an intervention on the ligaments.

According to an embodiment of the present invention, said palpation device has a ball shaped end and the locating by the palpation device is performed dynamically as said ball is displaced against the portion to be analyzed, the tridimensional positioning system being designed to determine the instantaneous positions of the ball center and a system of surface reconstitution from a deformable model being designed to perform a correction corresponding to the ball radius.

According to an embodiment of the present invention, an image of the adjusted model is formed and this image is displayed by assigning its various areas colors or thicknesses characterizing the density of points found in this area by the palpation device, which indicates the degree of accuracy of the model of the corresponding area.

According to an embodiment of the present invention, the system includes means for:

determining by calculation locations at which the tibia/femur must be drilled into to accommodate a section guide;
pointing these locations on the displayed image of the tibia/femur,
permanently displaying on the restored image of the tibia/femur the image of a drilling guide provided with locating means in said tridimensional, positioning system, this guide including tubes separated by the same interval as tubes of the section guide intended to be assembled on threads fixed in the bone,
and the drilling guide includes a central point that can bear against the bone and the image of which must coincide with a target point pre-positioned on the displayed image of the tibia/femur.

According to an embodiment of the present invention, the drilling guide further includes adjustment means, operable once the guide has been brought to its position.

According to an embodiment of the present invention, the locatable elements respectively associated with the tibia, with the femur and with the sensor are geometrically differentiated.

According to an embodiment of the present invention, the locatable element associated with the tibia has the shape of letter T, the locatable element associated with the femur has the shape of letter F, the locatable element associated with the palpation device has the shape of letter P.

According to an embodiment of the present invention, the position of the patella component of the prosthesis is obtained by means for:

determining in a tridimensional positioning system the trajectory of an element having a locatable position attached to the external surface of the patella in a knee flexion motion, determining the point of the internal patella surface which better coincides with the center of the groove of the prosthesis of the femur for a selected angular flexion area;

guiding the placing of a drilling thread towards said point.

The foregoing objects, features and advantages of the present invention will be discussed in detail in the following non-limiting description of specific embodiments in connection with the accompanying drawings.

Figure 1A:
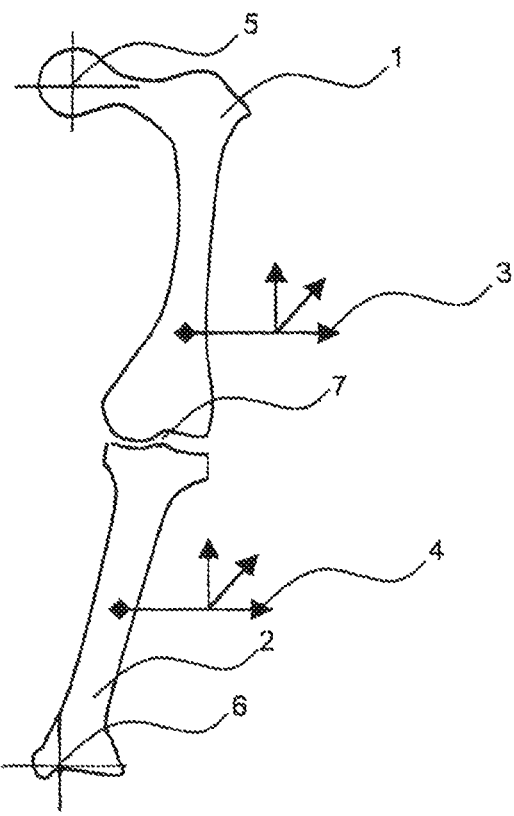
FIGS. 1A and 1B show a front view and a side view of a femur-tibia assembly.
Figure 1B:
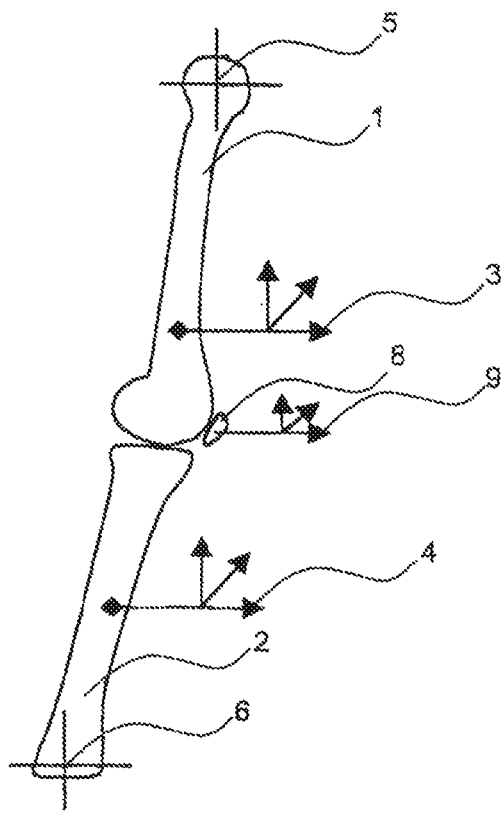
Figure 2A:
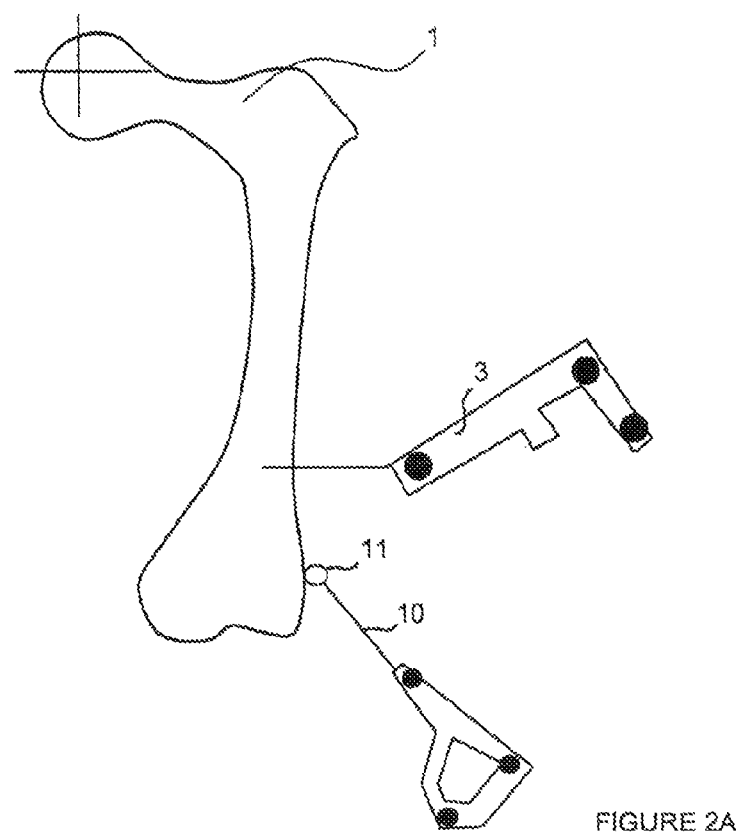
FIGS. 2A and 2B illustrate a femur and an associated sensor.

To perform an intervention according to the present invention, the bones are placed in the field of a tridimensional positioning system. Then, as illustrated in FIG. 1A in side view and in FIG. 1B in front view, elements locatable by the tridimensional positioning system respectively attached on femur 1 and on tibia 2 of a patient, respectively 3 and 4, are analyzed. These locatable elements are generally points screwed in the bones, one end of which is provided with markers which may be reflective disks, reflective spheres, or infrared diodes. As illustrated in FIG. 2A, to avoid any error risk, the present invention provides for locatable element 3 attached on the femur to be F-shaped, with at least three markers attached on the ends of the branches and on the corners of the F. This device enables having the largest possible letter, which avoids any possible confusion, with markers which are as distant as possible, which increases the system accuracy, while forming a compact shape. Similarly, the locatable element attached to the tibia is T-shaped with three markers attached to the ends of the branches of the T. All locatable elements may thus be associated with a letter, P for the palpation device, R for the patella, H for the humerus, etc. containing markers on the ends of its branches and on its corners.

Reference number 5 designates the center of rotation of the hip between the femur and the ilium, reference number 6 designates the center of the ankle between the tibia and the foot, and reference number 7 designates the joint of the knee between the femur and the tibia. In FIG. 1B, the patella has been designated with reference number 8 and a locatable element attached to the patella on its external surface has been designated with reference number 9.

The present invention provides using means for determining the deformation of a generic model to follow digitized points on the real bone. The model is generally formed of a set of several hundreds of triangular facets connected to one another on their edges and vortexes. Methods may be used, which are described in chapter 16 of book "Brain Warping", Toga ed., Academic Press, 1999, entitled "Elastic registration and Interference using Oct-Tree Splines", pages 282-296, S. Lavallee et al., consisting of deforming as little as possible a volume meshing which encompasses and drives along the digitized surface points to have them coincide with the model surface, then inverting the transformation function thus obtained to deform the generic model towards the digitized points. In such a method, it is first searched for a general deformation which brings some specific anatomic points palpated by the user to their homologous points of the model, after which the deformation is refined by progressively decreasing the sum of the squares of the distances between all the palpated points and the model surface. Methods of distance calculation between points and a surface represented by triangular facets are widely known in computerized tridimensional geometry literature. A deformation function F transforming the coordinates (X,Y,Z) of a point expressed in the position reference system into coordinates (X',Y',Z') of the point expressed in a reference system associated with the model is thus obtained. To obtain the deformed model, the antecedent point (X,Y,Z) of each point of the model (XM, YM,ZM) over function F is searched by iteratively minimizing the interval between (XM,YM,ZM) and F(X,Y,Z) and the geometric links applied between the model points. Methods described in article "Building a complete surface model from sparse data using statistical shape models: application to computer assisted knee surgery" by M. Fleute and S. Lavallee, published in Medical Image Computing And Computer-Assisted Intervention—MICCAI '98, Spinger-Verlag LNCS Series, pages 880-887, October 1998 may also be used. Such methods are robust since they use statistical models. An intelligent interpolation of the points enabling constructing complex surfaces by means of a few points, and thus easily and rapidly, is then achieved. The two mentioned approaches may also be combined by starting with searching for the deformation of a statistical model according to the method described in Fleute's previously mentioned article, then by carrying on with a deformation of a volume meshing according to the method described in S. Lavallee's article published in previously-mentioned book "Brain Warping".

To determine and digitize points on the bone surface, a palpation device locatable in the tridimensional positioning system is used. Conventionally, a palpation device with a pointed end may be used to obtain points on the surface with a good accuracy, but such a palpation device clings onto the bone and it is difficult to digitize many points on the fly.

Figure 2B:
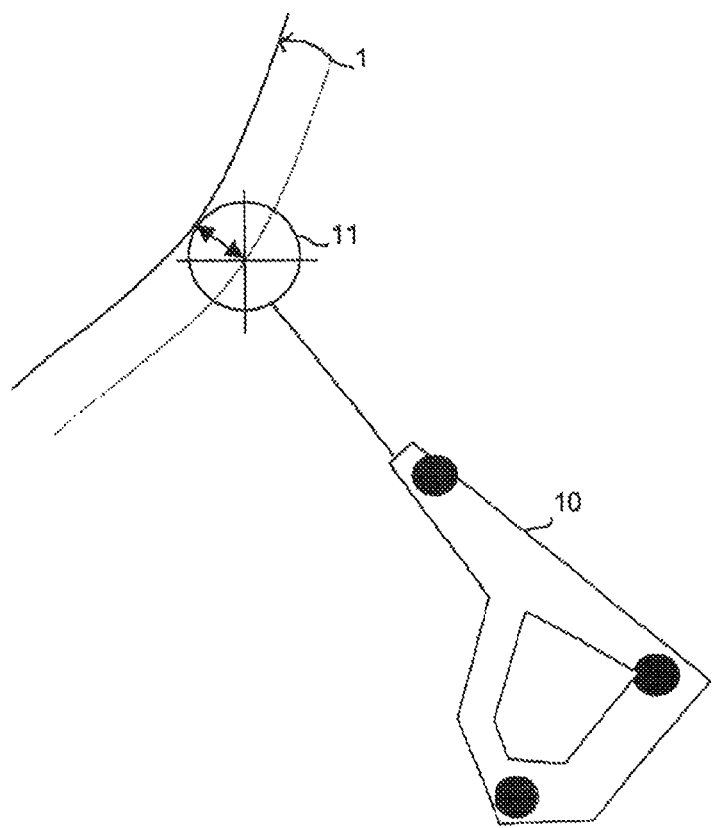

The present invention provides, as illustrated in FIGS. 2A and 2B, using a sensor 10 having its end in contact with the area to be detected including a specific portion with a radius that can be greater than 0.5 mm (preferably, from 0.5 mm to 3 mm). From a time when the surgeon or another operator sends an order by a pressure on a foot or hand control or by voice control, many points can then be digitized on the fly by sliding the spherical portion on the bone surface, but points shifted by a value equal to the radius of the sphere outside of the real surface are recorded. This shifting will have to be compensated for. To compensate for the sensor sphere radius, the present invention provides means for progressively minimizing the sum of the distances between each point and the model surface to which the value of the sensor radius is subtracted provided that the distances to the surface are positive outside of the surface and negative inside of the surface.

Despite the use of the sphere, it would be tedious to ask the operator to digitize all the useful parts of the bone surface. This may require a significant manual work and the reconstructed surfaces may be quite inaccurate, or even erroneous.

In cases where the surface points cannot be directly accessed to, an echographic probe equipped with a position mark may be used to locate points on the bone through the skin, as described in chapter 32 of book "Computer Integrated Surgery", MIT Press, 1996, R. Taylor ed., entitled "Computer-assisted spinal surgery using anatomy-based registration", pages 434-437, by S. Lavallee et al. The surface may also be constructed by using a few radiographic images obtained at the operating theatre suite or in the radiology room. If radiographs acquired outside of the operating suite are used, the models thus reconstructed must then be adjusted on the operating data. Such techniques are described in article "Nonrigid 3D/2D registration of images using statistical models" by M. Fleute and S. Lavallee, published in Medical Image Computing And Computer-Assisted Intervention—MICCAI '99, Spinger-Verlag LNCS Series 1679, pages 138-147, October 1999. This article also describes how to combine radiological information and position information to construct 3D surfaces.

Figure 3A:
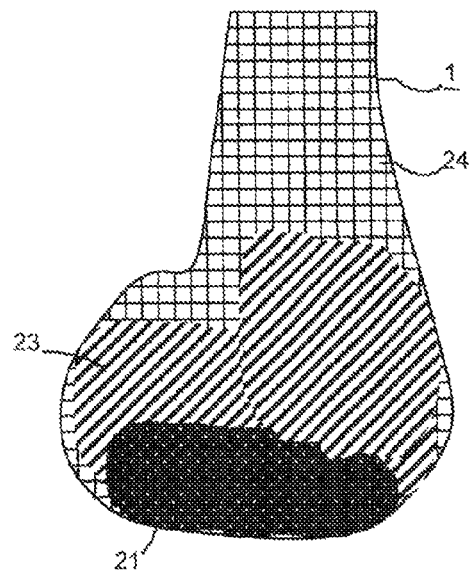
FIGS. 3A and 3B show a distal end portion of a femur and colored areas thereon.

The surface reconstructed by the deformation method cannot be perfect and inaccuracies remain, especially in regions where points have not been palpated. It is important for the surgeon to be informed of the inaccuracies of the surface reconstruction. As illustrated in FIG. 3A, to give an indication of this inaccuracy to the surgeon, the present invention provides displaying on a screen of the computer the surfaces reconstructed in 3 dimensions with, surface colorings according to the estimated inaccuracy. For example, in regions 21, which are critical for the prosthesis, where many points have been palpated, the surface is of a first color. In regions 22 and 23, which are less critical for the prosthesis, where less points have been palpated, the surface is of a second color. For the rest of the femur, in regions 24 where little or no sensing has been performed, the image is substantially that of the initial model at another scale factor and this is indicated by a third color. The portion of the surface contained in spheres of X mm around the digitized points may also be colored. More or less brightly colored areas are thus obtained according to the amount of sensing. A color gradation may be assigned according to the increasing values of X to obtain a continuous effect. The values of the inaccuracy of the reconstruction on the surface may be obtained by other means, what matters being to given a notion thereof to the surgeon.

Figure 3B:
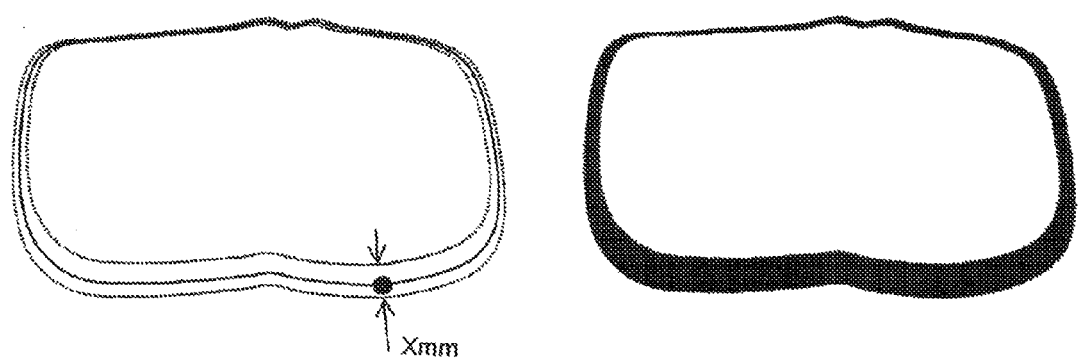

When a planar section of the reconstructed surface is displayed, inaccuracy colors may further be displayed on the portions of the intersection contours between the plane and the surface. Preferably, contours are displayed around the calculated intersection contour with a thickness depending all along the contour on the inaccuracy of the estimated surface in the considered region. As illustrated in FIG. 3B, if a point of the intersection contour between the plane and the surface has an inaccuracy of X mm, a thickness of X mm is given to the contour of this point.

Figure 4:
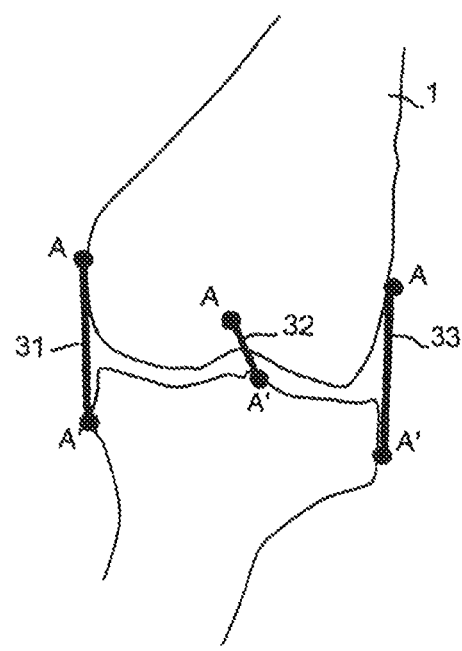
FIG. 4 shows a model of a femur-tibia assembly and of associated ligaments.

As illustrated in FIG. 4, it is known to define and construct models of the ligamentary structures (also including tendons, muscles, cartilages, and others) attached to the surfaces of the modeled bone structures. Such models are relatively faithful approximations of the reality which enable predicting the general behavior of the knee structures, according to the different positions of the prostheses, as described in article "A strain-energy model of passive knee kinematics of surgical implantation strategies" by E. Chen et al, published in Medical image Computing And Computer-Assisted Intervention—MICCAI '2000, Spinger-Verlag LNCS Series 1935, pages 1086-1095, October 2000. The main difficulty of known methods is the construction of the models adapted to each patient. The attachment points of the ligaments may be located on MRI images but this is inaccurate and tedious, it does not provide the elastic properties of the ligaments, and does not translate the general behavior of the knee including the sum of all unlocated minor structures. For simplicity, a model formed of a femur 1 and of a tibia 2 connected together by ligaments 31, 32, 33 is considered. For example, the lateral ligaments, the crossed ligaments and the ligaments of the rear capsule may be modeled by simple straight lines or elastic curves or else by pencils of straight lines or curves, with a maximum elongation for each straight line, curve or fiber. Having used the previously-described method to deform the model on the surface points digitized on the real bone, the result of the deformation may be applied to the attachment points of the ligamentary structures on each bone of the model so that they are now known in the reference system associated with each bone. Given the strong inaccuracies of the models and the strong variations of each individual, it would be inaccurate to use the elasticity parameters of the ligaments of the model and to apply them as such to the patient's data. To avoid such errors, prior to the intervention, once the position marks are in place in each bone, the surgeon or another operator exerts motions on the tibia in all possible directions and for several knee flexions to reach multiple extreme positions of the tibia with respect to the femur. The operator exerts strong but reasonable forces on the bones, to place the ligaments close to their maximum elongation. The computer memorizes all the relative positions of the tibia with respect to the femur during these motions. For each ligament connecting a point A of the femur to a point A' of the tibia, all the distances between points A and A' for each of the memorized relative positions are then calculated. Only the largest distance is retained. This distance is that corresponding to the maximum ligament length. At the end of this step, each ligament model is known by its two attachment points on the femur and on the tibia, as well as by its maximum length when extended. Based on the maximum length of the ligament in extended position, and assuming that the manual strain imposed to the ligament by the surgeon is approximately known, models known in biomechanics may be applied on the extension of the ligaments to assign them a nonlinear curve characterizing the elongation according to the tension strain, but such a very complete model will have to only remain qualitative and the maximum elongation model will generally be that used. In practice, the system according to the present invention includes means for memorizing the maximum extensions of the ligaments for different angular knee flexion areas to compensate for the errors linked to the position of the ligament attachments in each of these areas, these angular areas may be the area of a flexion from 0 to 10°, the area of a flexion from 10 to 30°, and the area of a flexion from 70 to 120°. For each area, it is also possible to only reconstruct the model of the ligaments which are known to be involved in this area.

To complete the acquisition of the data necessary for what follows, the position of the ankle center must be determined in the referential system of the tibia and the hip center must be determined in the referential system of the femur. For this last point, known methods are used, for example, the method described in French patent application PR-A-2785517 by P. Cinquin et al. entitled "Precede et dispositif de determination du centre d'une articulation". To determine the ankle center, the present invention provides digitizing characteristic points on the ankle and defining the ankle center by a geometric rule using these characteristic points, as a complement of the data acquired on preoperative radiographs. For example, the bumps of the internal and external malleolae may be palpated, after which the ankle center can be considered as the right-hand point with a relative distance equal to the relative distance measured on a front radiograph of the ankle.

The present invention provides using the various above-mentioned measurement and position determination means, to determine an ideal theoretical position of femoral and tibial implants. It should be clear that the sequence of the different steps may be modified in many ways according to each surgical technique.

Figure 5A:
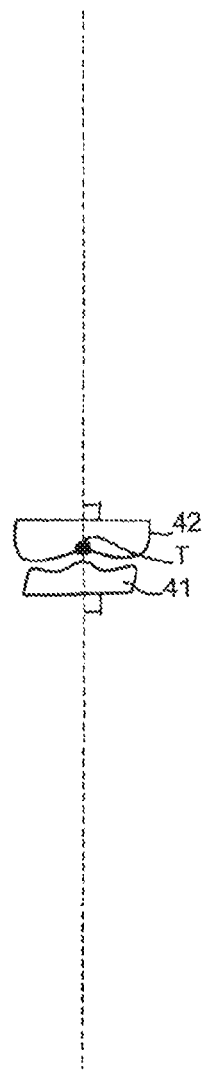
FIGS. 5A to 5C illustrate the assembly of a prosthesis according to the present invention.
Figure 5B:
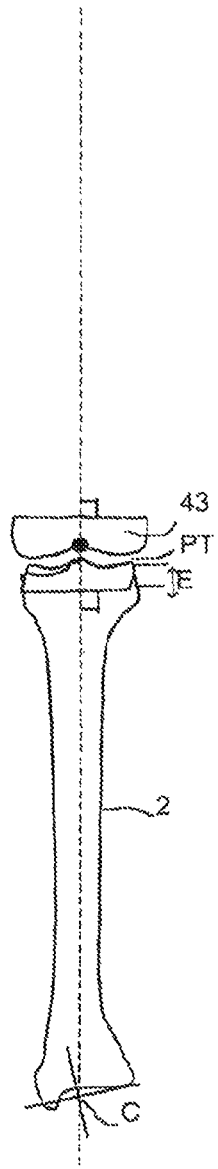
Figure 5C:
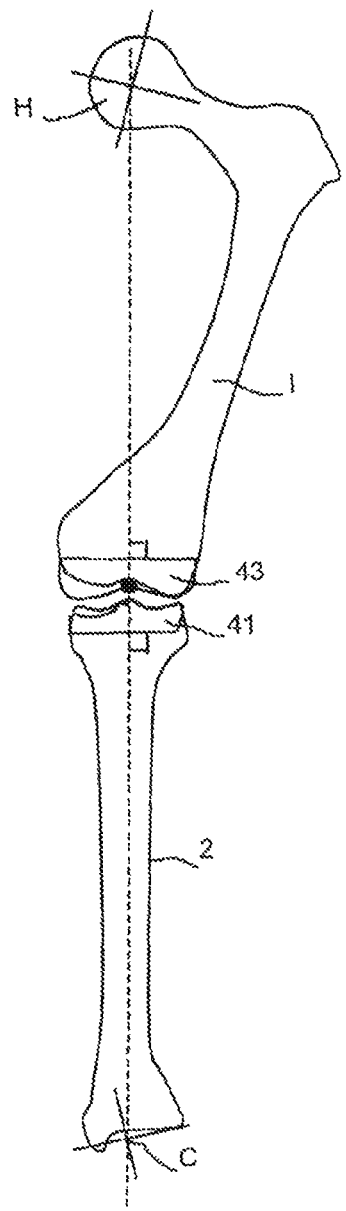

As illustrated in FIGS. 5A to 5C, the position of a portion of the prosthesis on a bone, for example, tibial prosthesis 41, is first set. Said prosthesis is generally formed of a fixed or mobile superior surface of a tibia 42, its position is defined by the 3 parameters defining a section plane and by the 3 parameters defining the position of the implant in the section plane (2 translations, 1 rotation). The implant size must also be chosen from among a wider or narrower range.

To begin with, the tibial prosthesis has a center T mechanically known by construction of the prosthesis. The tibial prosthesis also has a main plane which corresponds to the section plane on which it will bear. It is imposed as a constraint that the straight line crossing prosthesis center T and perpendicular to the section plane crosses the center of ankle C. The plane of the tibial prosthesis is then forced to be tangent to spheres centered on ankle center C. This constraint sets 2 of the 6 parameters.

Then, a reference point PT is palpated on the tibia and the section plane is placed at a distance E from point PT, the value of E being equal to the thickness of the superior surface of the tibia. This constraint sets 1 of the 6 parameters.

There remains to determine the ideal position of the implant in the section plane. A horizontal axis of the knee is first determined either by searching the rotation axis between the two extreme flexion and extension positions of the knee, or by connecting two specific anatomic points such as the epicondyles, defined by direct palpation or defined on the model adjusted to the patient. The angle between this knee axis and the axis of the tibial prosthesis is established by default at 0°. The two remaining translation parameters are set to respect a geometric bulk in each considered section plane.

Figure 6A:
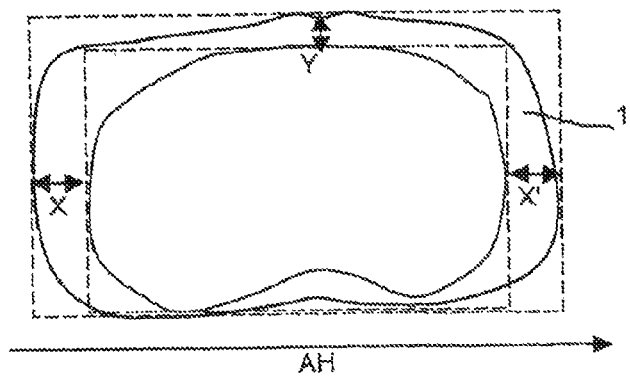
FIGS. 6A to 6C illustrate steps implemented by the system according to the present invention.

As illustrated in FIG. 6A, for the smallest given prosthesis size, an arbitrary initial position of the prosthesis is given, and the intersection contours between the surface and the corresponding section plane are calculated and compared to the prosthesis contour in this plane. For each of the two contours, the rectangle of minimum size encompassing all the contour points is calculated, imposing an orientation of an edge of the rectangle parallel to horizontal axis AH. The intervals between the edges of each of the two rectangles are minimized, which gives a new position of the prosthesis in the section plane, and this process is repeated until it converges. The values of X and X' are thus measured between the lateral edges of the prosthesis and the lateral edges of the contour of the section on the surface, and the lateral position is adjusted to equalize X and X'. Similarly, the distance from back to front Y is adjusted so that the prosthesis comes at Y mm from the anterior edge of the intersection contour, Y being a value set by default by the surgeon. The entire process is repealed, searching for the largest size for which all edges of the prosthesis are inside of the edges of the intersection contour, including the posterior edges. The position, the size and the orientation of the tibial prosthesis are thus totally automatically determined. If need be, the operator may then move each of the parameters, preferably by means of a tactile screen (or any other mouse equivalent), to align on values of his choice according to each surgical technique recommendation.

Figure 6B:
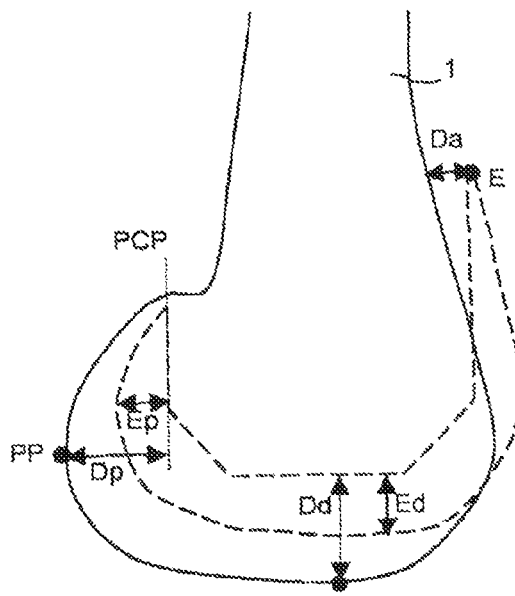

The position of the femoral prosthesis is determined in an approximately equivalent manner, taking into account center H of the hip instead of the ankle center. As illustrated in FIG. 6B, the anteroposterior position of the prosthesis is automatically calculated to equalize thickness Ep of the posterior condyle of the prosthesis with distance Dp calculated between the posterior section plane of prosthesis PCP and the most posterior point PP of the surface of one of the two posterior condyles of the knee selected by the surgeon. Posterior point PP is automatically determined by the computer as being the point of the condyle considered on the model and adapted to the patient having the smallest coordinate Y in the direction of a vector Y from the posterior to the anterior. This principle is applicable to the search for all the endmost points in a given direction. The size of the largest prosthesis is determined by the computer so that the distance between the endmost point E which is most proximal to the prosthesis is close to the femur surface while remaining inside of this surface. This criterion is fulfilled by iteratively minimizing the distance between the endmost point of the memorized prosthesis and all the triangular facets forming the surface. The distal position of the prosthesis is determined by the computer to equalize the thickness of the distal condyle of prosthesis Ep with distance Dp calculated between the distal section plane of the prosthesis and the most distal point of the surface of one of the two distal condyles of the knee selected by the surgeon.

To adjust the lateral position of the femur prosthesis, the lateral edges may be used as described for the tibia. Preferentially, the present invention provides memorizing the trajectory of the midpoint R of the patella surface in a knee flexion motion, starting with the complete extension. A small and light position mark attached on the external portion of the patella by means of small thin and shallow pins is used for this purpose. For a position of patella 8 closed on femur 1 (obtained for example at the beginning of the operation), the motions of the patella mark with respect to the femur are recorded. Point R thus describes a trajectory which is known in the femur reference system. The femur prosthesis contains a groove to accommodate the patella during the knee flexion. The middle of the groove is in a plane.

Figure 6C:
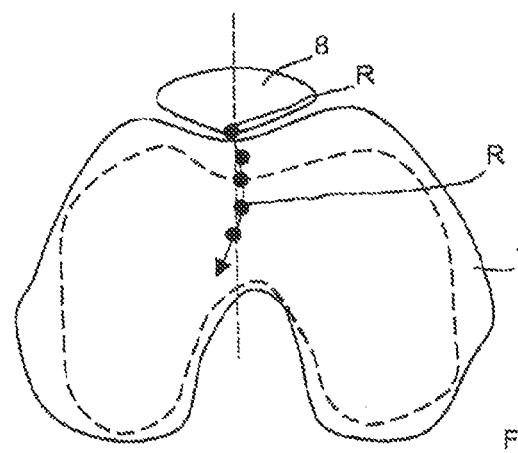

As illustrated in FIG. 6C, the position of the femur prosthesis is determined to have the plane of the groove coincide at best with the trajectory of point R. A rotation parameter may be used to optimize this alignment. To optimize all criteria at the same time, the process starts from an empirically-determined arbitrary initial position close to the searched solution, then the criteria are minimized one by one by modifying the value of the position, orientation, or size parameter of the prosthesis which influences it most, iteratively, until obtaining a stable convergence of the ideal position, orientation and size of the implant. When several parameters influence a criterion, multidimensional optimization methods well known in mathematical literature are used.

Up to now, it has been assumed that the positions of the tibia and of the femur were independent. In reality, the prostheses of the femur and of the tibia are designed by defining an ideal trajectory of the tibial prosthesis on the femoral prosthesis from flexion to extension, at least for 3 or 4 flexion positions, for example, 0°, 30°, 90°, and 120°. For each of these angles, the ideal relative position between the femoral component and the tibial component of the prosthesis is totally determined. Some prostheses are said to be non-congruent and allow for more complex motions than a simple trajectory of flexion of the tibial component with respect to the femoral component but the average neutral kinematics significantly describe an ideal searched component, it being also possible for the method implemented by the present invention to take into account the intervals with respect to the neutral kinematics. At this stage, all the relative positions of the implants and of the bones for different motions chosen according to the considered prosthesis can thus be simulated. The model then enables predicting that the ligaments do not exceed their limiting value for all these relative positions. If some ligaments exceed their limits, the surgeon may use this information to provide surgically relaxing the ligament. At any time, the surgeon can intervene on the ligaments and randomly acquire again the extreme positions to recalibrate the parameters of the ligaments and restart the prediction.

For any global position, the present invention provides simulating relative motions of the tibia and of the femur by rotations around contact points existing on the condyles to simulate positions in which the ligaments are in maximum elongation when forces approximately equivalent in intensity and direction to the forces applied upon measurement of the maximum elongations of the ligaments are applied. The ligamentary balance can thus be predicted for different flexion angles characterized by the amplitude of the motions and by the dissymmetry of the possible motions around the neutral position.

The surgeon can then freely determine the essential parameters which most influence the setting of the ligamentary balance, without having made any bone section yet. He can for example choose to keep a perfect alignment of the hip and ankle centers with the prosthesis center in extension, but inclining the line perpendicular to the section planes with respect to the mechanical axis, thus creating oblique interlines between the prostheses. Any type of surgical technique can thus be simulated by using the system according to the present invention.

Once each section plane of a bone (tibia or femur) has been determined, it is provided to attach to this bone a section guide in which a saw blade is engaged to perform the section with accuracy according to the angle determined by the computer (possibly altered by the surgeon). A section guide generally includes at least two cylindrical bushes enabling placing threads fixed in the bone. A section guide is a relatively bulky and heavy instrument, and supports adjustable with screws, wheels or wedges to hold and place these section guides generally have to be used, said supports being themselves attached to the patient by various rods which are heavy, bulky and often invasive, that is, significantly deteriorating the bone in its healthy parts. Ideally, it would be desired to be able to avoid using such supports and place the section guides directly, but this is very difficult to perform manually. The direct alignment of a plane on an ideal plane or of a solid on an ideal solid is a delicate operation, even using visual alignments on a screen which shows the real and desired positions of each structure according to various graphical representation modes. The present invention, instead of trying to directly position a section guide, provides previously using a drilling guide including two cylindrical bushes having exactly the same spacing as those of the cross-section guide and a punctual point used as a mechanical constraint.

Figure 7:
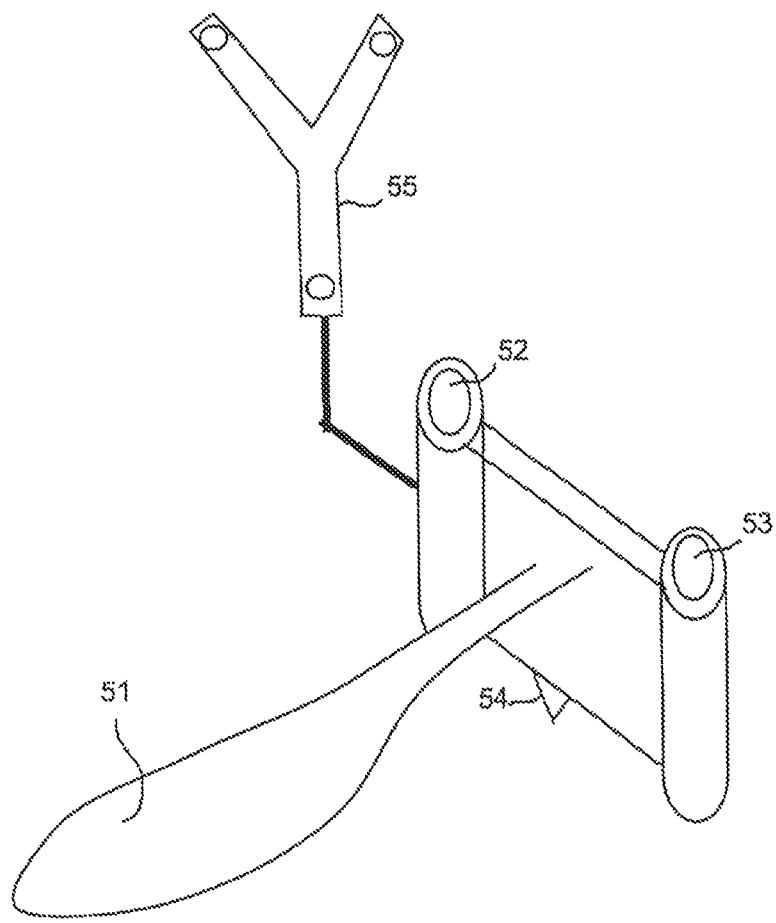
FIG. 7 shows a drilling tool according to the present invention.
Figure 8:
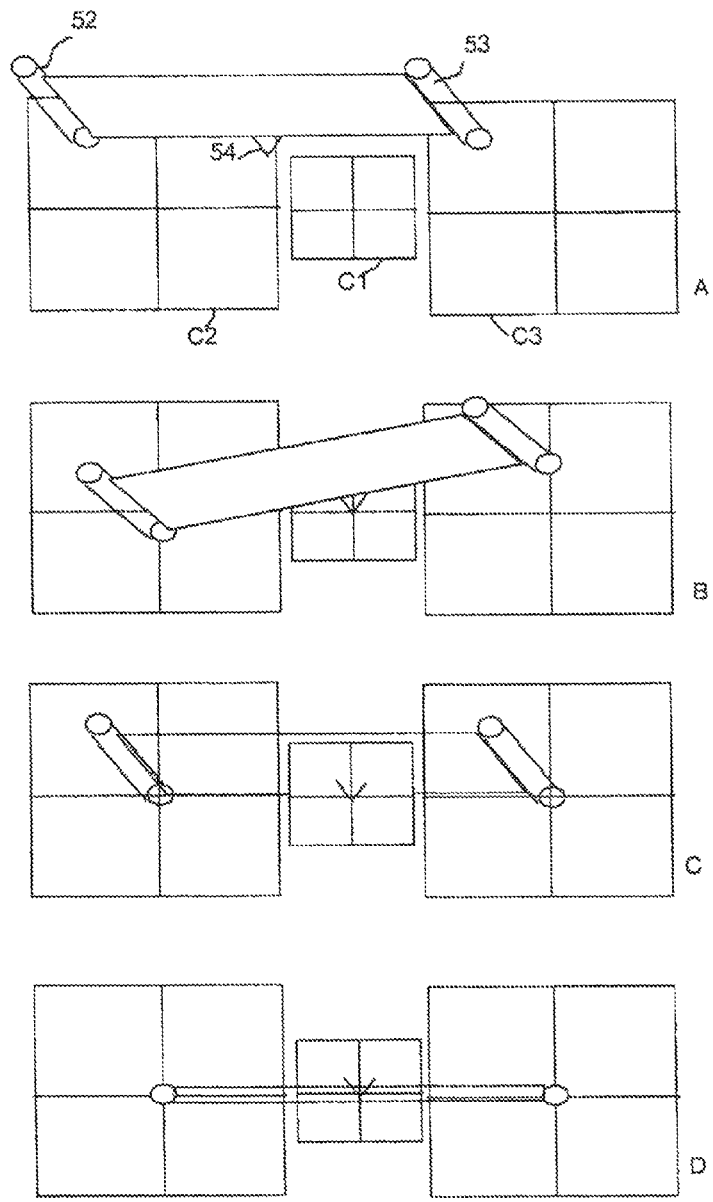
FIG. 8 shows targets for determining the position of a drilling object according to the present invention.

FIG. 7 shows a drilling guide according to an embodiment of the present invention. This drilling guide includes a handle 51. The two cylindrical bushes are designated by references 52 and 53. To this drilling guide is rigidly associated a position mark 55 visible by the tridimensional positioning system monitoring the operation scene. Mark 55 is for example provided with 3 reflective markers and is Y-shaped. According to a significant feature of the present invention, the drilling guide includes a pointed point 54. The general shape of this drilling guide, that is, the relative position of point 54 and of bushes 52 and 53 in the Y-shaped position mark is memorized in the computer used to determine the position and the orientation of the section plane with respect to the considered bone. As shown in FIG. 8, this computer displays a target including a central target C1 and lateral targets C2 and C3. The display of target C1 is a parallel perspective view in the direction of the point axis. The display of targets C2 and C3 are parallel perspective views in the direction of the hush axis. First, the image of point 54 must be brought exactly on the center of target C1. The point must for this purpose be slid on the bone surface according to two translations, which is easy. Once the good position of the point has been found, the point is very slightly driven into the bone so that if remains stable thereafter. All the guide motions are then forced to turn around this fixed point. The images of bushes 52 and 53 are then brought on lateral targets C2 and C3, which is easily done by setting three rotations around a fixed and mechanically stable point. These operations are performed by the surgeon or another operator by displacing the drilling guide on the bone and by monitoring its image on the computer which substantially appears as shown in FIG. 8A. Thus, at the step of FIG. 8B, point 54 is put in contact with central target 61. At the step of FIG. 8C, bushes 52 and 53 are brought in front of targets C2 and C3 and, at the step of FIG. 8D, the bushes are placed according to the proper vertical orientation. Once the drilling guide is in position, threads inserted in bushes 52 and 53 are fixed in the bone.

Figure 9:
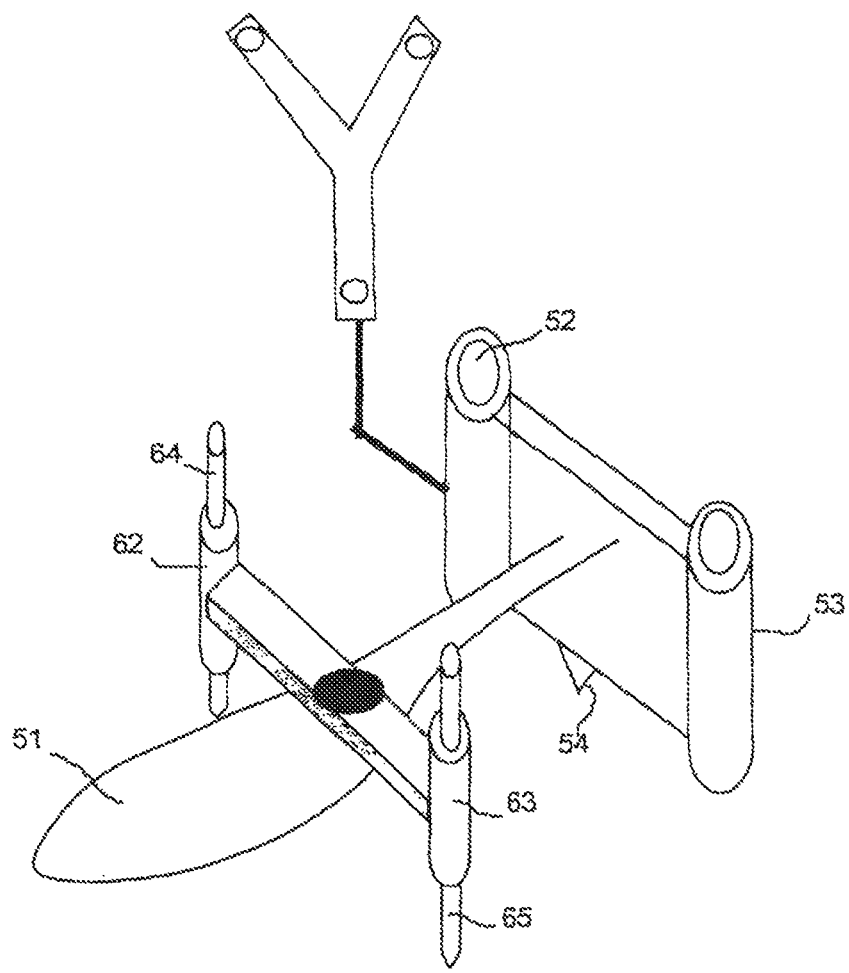
FIG. 9 shows an alternative of the drilling tool according to the present invention.

FIG. 9 shows an alternative of the drilling guide of FIG. 7 provided with means for blocking in position to avoid any sliding upon placing of the threads in the bone. For this purpose, on handle 51 is assembled a horizontal frame 61 which carries at its two ends, on either side of handle 51, two auxiliary vertical bushes 62 and 63. Each of bushes 62, 63 receives a pointed rod, respectively 64, 65 which crosses this bush. Inside of frame 61 is provided a blocking means operated by a button 67. Such a blocking can be performed by a spring which maintains a pressure on the rods. When the button is pressed, rods 64, 65 freely slide in bushes 62, 63. Thus, they come down until stopping against the bone above which they are placed. As soon as button 67 is released, the rods are blocked in position. The surgeon, as soon as he has reached the position illustrated in FIG. 8D, can then, without having to keep on monitoring the target appearing on the computer screen, assemble the threads while being ensured that the drilling guide does remain in its position, since it bears upon 3 fixed points.

Once the drilling threads are positioned in the bone, the drilling guide is removed and the first section guide is assembled on the threads which have just been set. For a prosthesis such as the femur which includes several section planes, a series of section guides calibrated to perform all sections corresponding to the bearing planes of the prosthesis, propping up against the two reference threads placed in the bone, may then be added. For each of these section guides, the relative position of the two bushes intended to contain the holding threads and the section planes is precisely known. It is important to note, on this regard, that the point imposes a degree of liberty of the section guides since it is in contact with the surface. The choice of the point position is thus very important since it conditions the final position of the prosthesis.

Figure 10:
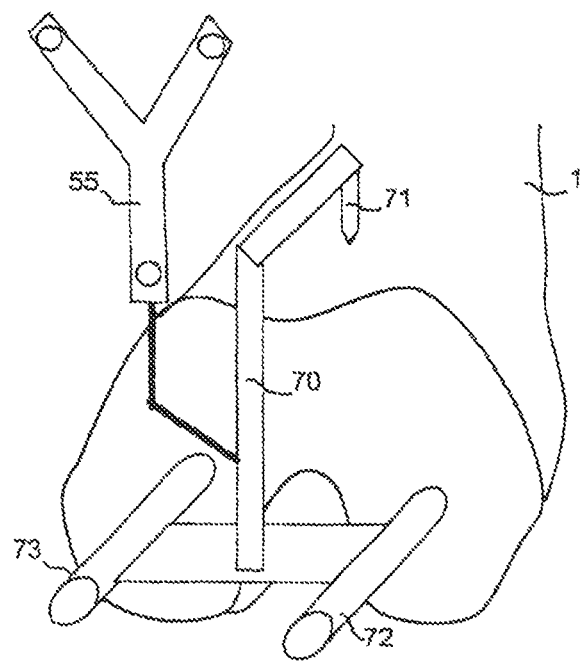
FIG. 10 shows another alternative of the drilling tool according to the present invention.

FIG. 10 shows another drilling guide 70 specifically applicable to the femur prosthesis in which the holding point 71 is off-centered with respect to the drilling bushes 72, 73, to bear against the anterior surface of femur 1, to mechanically force the drilling guide to respect the anterior position of the prosthesis to be with accuracy.

Figure 11:
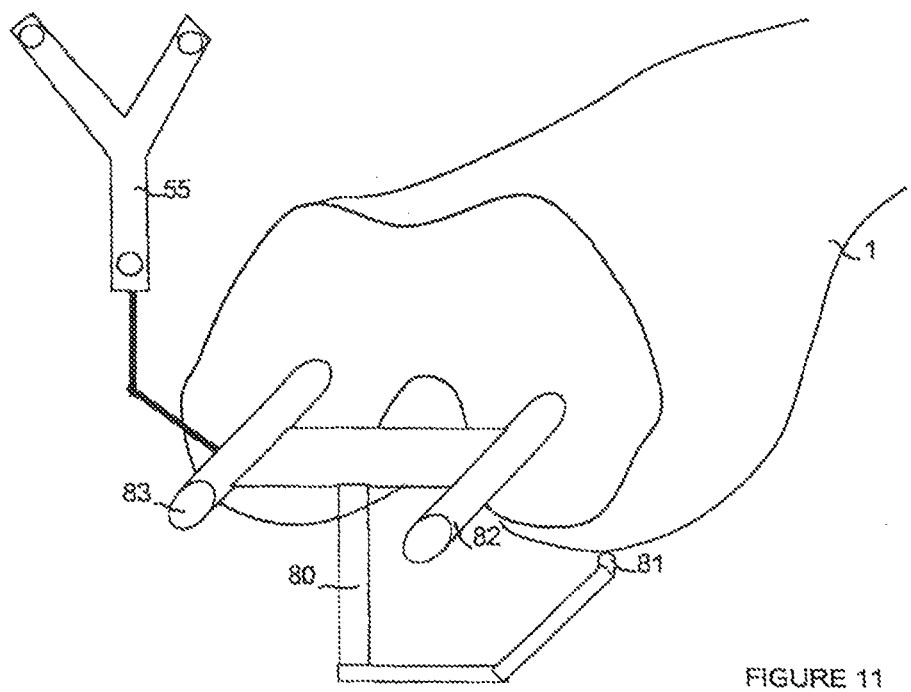
FIG. 11 shows another alternative of the drilling tool according to the present invention.

FIG. 11 shows another drilling guide 80 specifically applicable to the femur prosthesis in which holding point 81 is off-centered with respect to drilling bushes 82, 83 to bear against the posterior surface of one of the two condyles of femur 1, to mechanically force the drilling guide to respect the posterior position of the prosthesis to be with accuracy.

Of course, this structure is likely to have various alterations and modifications which will occur to those skilled in the art. For example, several points and a single blocking rod could be provided. All the drilling guides described in the present invention will be made in shapes and materials to be as light as possible, to be easily handled.

Once a number of section planes have been formed, wedges can be introduced between the femur and the tibia bearing against these sections at the level of the two condyles of the femur to check that the ligamentary balance will be correct once the prostheses have been placed. Conventionally, the surgeon mechanically displaces the tibia from left to right to evaluate its angular play, but this measurement remains inaccurate. The system according to the present invention enables accurately measuring the angular variation and displaying it on the computer screen. The two signed angles Bd and Bg obtained by an extreme displacement to the left and to the right with respect to the neutral position of the knee at rest are displayed. The difference between the absolute values of the two angles Bd and Bg is a measurement of the ligamentary imbalance from left to right. The sum of the absolute values of angles Bd and Bg is a measurement of the general ligamentary balance. Indicators Bd+Bg and Bd−Bg are measured and displayed for various flexion angles. Preferentially, angles Bd and Bg are graphically shown on a screen in a vertical segment of a straight line corresponding to the neutral position and by two segments intersecting the neutral segment at its vertex and forming angular values of Bd and Bg with the neutral segment. By means of these measurements, the surgeon can extend or relax the ligaments, or add or subtract thicknesses between the prostheses of the femur and of the tibia to obtain a good balance for all degrees of flexion.

According to another preferential embodiment, the present invention provides displaying the distances between the closest points facing one another on the femur and on the tibia equipped with their simulated or real prosthesis, for each of the two condyles, and for several flexion angles, when the knee is submitted to external stress of swinging from left to right.

Once the femoral prosthesis is in place, many surgical techniques invite to place a small prosthesis of button type on the internal surface of the patella. The system according to the present invention enables determining the ideal position of this patellar button. The position of the groove of the femoral prosthesis may be determined in the position reference system associated with the femur, either by using the previously predicted position, or by digitizing in fine the groove by palpation on the fitted prosthesis. The relative positions of the position mark attached to the patella are known and memorized for several flexion angles. For a chosen flexion position, the digitized groove position can then be displayed on screen by projecting it on a view corresponding to the internal patella surface. Or conversely, the patella trajectory obtained for all flexions can be obtained according to an axial or front view of the femur trochlea. After having conventionally cut the patella across its thickness, the surgeon can then use a drilling guide and aim at a point on the internal surface of the patella which coincides with the groove on the femur, either globally, or for a given angular flexion area, so that the patella does penetrate at the middle of the groove towards 20 degrees of flexion, and to balance the lateral forces which will be exerted between the patella and the femoral prosthesis. This drilling into the bone will then be used as a centering to place the final patellar button.

The method and the system described in the present invention may be applied to any type of knee prosthesis and they are compatible with most surgical knee prosthesis setting techniques, and they may be extended to other joints such as the elbow or the shoulder.

I claim:

1. A method for determining a position of a joint prosthesis using a computer assisted orthopedic surgery system in support of an arthroplasty surgery of a joint of a patient comprising:
    attaching a first locatable element to a first bone on one side of the joint;
    providing a sensor comprising a second locatable element;
    moving the sensor in proximity of the joint, wherein a plurality of positions on the first bone is located by locating a plurality of positions of the sensor relative to the first locatable element using a tracking device;
    selecting a generic model of a joint that is not specific to the patient;
    deforming, with the use of a computer, the generic model in response to the plurality of positions located on the first bone of the joint;
    determining an initial position of a joint prosthesis on the deformed model;
    determining a section plane in the deformed model corresponding to the initial position of the joint prosthesis;
    determining a contour between a surface of the deformed generic model and the section plane; and
    displaying the contour of the deformed generic model on a display.

2. The method of claim 1, further comprising:
    (a) determining a contour of the joint prosthesis at the section plane; and
    (b) displaying the contour of the joint prosthesis alongside the contour of the deformed generic model.

3. The method of claim 2, further comprising:
    (c) selecting an initial size of the joint prosthesis;
    (d) determining if all edges of the contour of the joint prosthesis are inside all edges of the contour of the deformed generic model; and
    (e) repeating steps (a), (b) and (d) for a subsequent joint prosthesis until a largest size joint prosthesis is determined for which all edges of the contour of the joint prosthesis are inside all edges of the contour of the deformed generic model.

4. The method of claim 2, further comprising determining a maximum size of the joint prosthesis based on the displayed contours.

5. The method of claim 4, wherein the maximum size of the joint prosthesis is defined as a size wherein all edges of the contour of the joint prosthesis are inside all edges of the contour of the deformed generic model.

6. The method of claim 2, further comprising:
    defining a first rectangle of minimum size encompassing all contour points of the deformed generic model and a second rectangle of minimum size encompassing all contour points of the joint prosthesis;

orienting an edge of the first and second rectangles to be parallel to a horizontal axis; and determining intervals between edges of the first and second rectangles.

7. The method of claim 1, further comprising:

determining a distance between the contour of the deformed generic model and the joint prosthesis about opposite sides of the first bone; and repositioning the joint prosthesis on the deformed model to equalize the distances between the contour of the deformed generic model and the joint prosthesis about opposite sides of the first bone.

8. The method of claim 1, further comprising determining a maximum size of the joint prosthesis based on the displayed contour of the deformed generic model.

9. The method of claim 1, wherein the joint is a knee joint that includes a femur and a tibia and the joint prosthesis is a femoral component or a tibial component.

10. The method of claim 1, further comprising:

determining an accuracy of the deformed generic model based upon a density of the plurality of positions located; and displaying the accuracy of the deformed generic model using at least one of various colors and line thicknesses.

11. The method of claim 1, wherein the joint is one selected from the group consisting of a knee joint, an elbow joint and a shoulder joint.

12. The method of claim 1, wherein the section plane is a horizontal section plane.

13. The method of claim 1, wherein the tracking device is at least one selected from the group consisting of a camera, a magnetic tracker, a mechanical tracker, and an acoustic tracker.

14. The method of claim 1, wherein the sensor is selected from the group consisting of a palpation device, an echographic device, a radiographic device, and combinations thereof.

15. A method for determining a position of a joint prosthesis using a computer assisted orthopedic surgery system in support of an arthroplasty surgery of a joint of a patient comprising:

attaching a first locatable element to a first bone on one side of the joint;

providing a sensor comprising a second locatable element;

moving the sensor in proximity of the joint, wherein a plurality of positions on the first bone is located by locating a plurality of positions of the sensor relative to the first locatable element using a tracking device, selecting a generic model of a joint that is not specific to the patient;

deforming, with the use of a computer, the generic model in response to the plurality of positions located using the tracking device;

determining an initial position of a joint prosthesis on the deformed model;

determining a section plane in the deformed model corresponding to the initial position of the joint prosthesis;

determining a contour between a surface of the deformed generic model and the section plane and a contour of the joint prosthesis at the section plane; and displaying the contour of the joint prosthesis alongside the contour of the deformed generic model on a display.

16. The method of claim 15, further comprising:

determining an accuracy of the deformed generic model based upon a density of the plurality of positions located; and displaying the accuracy of the deformed generic model using at least one of various colors and line thicknesses.

17. A method for determining a size of a femoral joint prosthesis using a computer assisted orthopedic surgery system in support of an arthroplasty surgery of a knee joint of a patient comprising:

selecting a generic model of a knee joint that is not specific to the patient;

deforming, with the use of a computer, the generic model in response to a plurality of positions located on a first bone of the joint;

determining an initial position and size of a femoral joint prosthesis on the deformed model;

calculating a distance value between an anterior aspect of the selected size femoral joint prosthesis and a surface of the deformed model; and displaying on a display the size of the femoral joint prosthesis and the calculated distance valve between the anterior aspect of the selected size femoral joint prosthesis and the surface of the deformed model.

18. The method of claim 17, further comprising determining an optimal size femoral joint prosthesis by iteratively minimizing the distance value between the anterior aspect of the femoral joint prosthesis and the surface of the deformed model of the knee joint.

19. The method of claim 18, wherein the step of iteratively minimizing the distance value includes selecting a subsequent larger sized femoral joint prosthesis and calculating a distance value between an anterior aspect of the subsequent larger size femoral joint prosthesis and the surface of the deformed model.

20. The method of claim 17, wherein the distance value between the anterior aspect of the femoral joint prosthesis and the surface of the deformed model of the knee joint is calculated at an endmost proximal point of the femoral joint prosthesis.

21. The method of claim 17, wherein the femoral joint prosthesis is initially positioned based upon at least one posterior condyle of the deformed model of the knee joint.

22. The method of claim 21, wherein the initial positioning of the femoral joint prosthesis is based upon a most posterior point on the condyles of the deformed model of the knee joint.

* * * * *